United States Patent
Jost et al.

[19]

[11] Patent Number: 6,090,080
[45] Date of Patent: *Jul. 18, 2000

[54] INJECTION DEVICE FOR INJECTION OF LIQUID

[75] Inventors: Stefan Jost, Bolligen; Christoph Renggli, Bern; Hans Burkhardt, Solothurn, all of Switzerland

[73] Assignee: Disetronic Licensing AG, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 09/029,671

[22] PCT Filed: Jul. 5, 1996

[86] PCT No.: PCT/CH96/00249

§ 371 Date: Apr. 10, 1998

§ 102(e) Date: Apr. 10, 1998

[87] PCT Pub. No.: WO98/01172

PCT Pub. Date: Jan. 15, 1998

[51] Int. Cl.[7] ....................................................... A61M 5/00
[52] U.S. Cl. ............................ 604/207; 604/187; 604/218
[58] Field of Search .................................. 604/131, 134, 604/135, 181, 187, 207, 208, 209, 210, 211, 218, 220, 232, 234, 97, 98, 99

[56] References Cited

U.S. PATENT DOCUMENTS

| | | | |
|---|---|---|---|
| 4,592,745 | 6/1986 | Rex et al. | 604/211 |
| 4,865,591 | 9/1989 | Sams | 604/186 |
| 4,883,472 | 11/1989 | Michel . | |
| 4,946,446 | 8/1990 | Vadher . | |
| 4,973,318 | 11/1990 | Holm et al. . | |
| 5,017,190 | 5/1991 | Simon et al. . | |
| 5,084,060 | 1/1992 | Freund et al. | 606/192 |
| 5,114,406 | 5/1992 | Gabriel et al. . | |
| 5,244,465 | 9/1993 | Michel | 604/208 |
| 5,279,579 | 1/1994 | D'Amico . | |
| 5,279,585 | 1/1994 | Balkwill | 604/207 |
| 5,292,314 | 3/1994 | D'Alessio et al. . | |

(List continued on next page.)

FOREIGN PATENT DOCUMENTS

| | | |
|---|---|---|
| 0037696 | 3/1981 | European Pat. Off. . |
| 0058536 | 8/1982 | European Pat. Off. . |
| 0245312 | 10/1986 | European Pat. Off. . |
| 0268191 | 11/1987 | European Pat. Off. . |
| 0298067 | 6/1988 | European Pat. Off. . |
| 0327910 | 1/1989 | European Pat. Off. . |
| 0373321 | 6/1990 | European Pat. Off. . |
| 0496141 | 1/1991 | European Pat. Off. . |
| 0516473 | 5/1992 | European Pat. Off. . |
| 0498737 | 8/1992 | European Pat. Off. . |
| 0554995 | 8/1993 | European Pat. Off. . |
| 0594349 | 4/1994 | European Pat. Off. . |
| 0627229 | 5/1994 | European Pat. Off. . |
| 2701211 | 8/1994 | France . |
| 3638984 | 11/1986 | Germany . |
| 3645245 | 11/1986 | Germany . |
| 3900926 | 8/1989 | Germany . |
| 4223958 | 7/1992 | Germany . |
| 9305835 | 8/1932 | WIPO . |
| 9504563 | 2/1965 | WIPO . |
| 8702895 | 5/1987 | WIPO . |
| 9110460 | 7/1991 | WIPO . |
| 9218179 | 10/1992 | WIPO . |
| 9316740 | 9/1993 | WIPO . |
| 9409841 | 5/1994 | WIPO . |
| 9415210 | 7/1994 | WIPO . |
| 9501812 | 1/1995 | WIPO . |
| 9607443 | 3/1996 | WIPO . |

*Primary Examiner*—Wynn Wood Coggins
*Assistant Examiner*—Loan H. Thanh
*Attorney, Agent, or Firm*—Dorsey & Whitney LLP

[57] ABSTRACT

Injection device for injecting fluid from a fluid container equipped with a piston, comprising an actuating device having a rod-shaped driven member having a structured surface, a control button being movable in axial direction, and a hollow cylindrical counter component having a structured internal sleeve, said counter component matching the rod-shaped driven member and being coaxially arranged in relation to said driven member.

9 Claims, 4 Drawing Sheets

U.S. PATENT DOCUMENTS

| | | | |
|---|---|---|---|
| 5,295,976 | 3/1994 | Harris . | |
| 5,336,183 | 8/1994 | Greelis et al. | 607/97 |
| 5,338,311 | 8/1994 | Mahukar . | |
| 5,370,629 | 12/1994 | Michel et al. | 604/207 |
| 5,472,430 | 12/1995 | Vaillancourt . | |
| 5,496,293 | 3/1996 | Huggenberger . | |
| 5,514,097 | 5/1996 | Knauer . | |
| 5,527,294 | 6/1996 | Weatherford et al. . | |
| 5,549,558 | 8/1996 | Martin . | |
| 5,549,575 | 8/1996 | Giambattista et al. . | |
| 5,573,510 | 11/1996 | Isaacson . | |
| 5,582,598 | 12/1996 | Chanoch . | |
| 5,591,136 | 1/1997 | Gabriel . | |
| 5,591,138 | 1/1997 | Vaillancourt . | |
| 5,593,390 | 1/1997 | Castellano et al. . | |
| 5,609,577 | 3/1997 | Haber et al. . | |
| 5,643,214 | 7/1997 | Marshall et al. . | |
| 5,658,259 | 8/1997 | Pearson et al. . | |
| 5,674,204 | 10/1997 | Chanoch . | |
| 5,679,111 | 3/1995 | Hjertman et al. . | |
| 5,725,508 | 3/1998 | Chanoch et al. . | |
| 5,728,074 | 3/1998 | Castellano et al. . | |
| 5,743,889 | 4/1998 | Sams . | |
| 5,807,346 | 9/1998 | Frezza . | |

INJECTION DEVICE FOR INJECTION OF LIQUID

RELATED APPLICATIONS

This application claims the priority of PCT Application No. PCT/CH96/00249, filed Jul. 5, 1996, which is incorporated herein by reference.

The present invention relates to an injection device for injecting fluid according to the preamble of claim 1.

Syringe-shaped injection devices for injecting fluids have been known for some time. They contain a bushing-shaped main body which can be screwed together at approximately the centre and can be divided into two main sections:

a distal section (facing away from the patient) containing the discharge mechanism and comprising at least one rod-shaped driven member having a structured surface (e.g. a screw rod), a hollow cylindrical counter component corresponding to the driven member, provided with a structured internal sleeve (e.g. a screw nut) and a control button; and a proximal section (facing the patient) containing the fluid to be administered and a movable piston.

At the proximal end of the main body, a needle and a needle holder are attached, allowing the fluid to be discharged from the device; known needles of this type are for instance PENFINE® needles as described in WO95/01812.

The connecting member between the proximal and the distal section of the main body is the driven member, shifting the piston by the required dose in proximal direction and discharging the fluid through the needle.

Often the fluid to be injected is not directly contained in the main body but in an ampoule, with the fluid being stored between a piercable membrane and a piston displaceable by sliding.

Depending on the injection device, various features are expected from the discharge mechanism. There are devices allowing only a single discharge, devices allowing several discharges of the same dose and devices allowing freely selectable discharges.

For patients using injection devices allowing a change of ampoules, it is—irrespective of the complexity of the discharge mechanism—extremely difficult to wind back the driven member to the initial position in order to make the device ready for operation after the ampoule has been changed. Devices requiring the driven member to be rewound by the control button are known from WO93/16740. Devices allowing the threaded rod to be pushed back, as in publications U.S. Pat. No. 4,592,745 and EP-A-0 554 995, are more easily operated by patients. The disadvantage of these prior art devices is that due to the release of the distal section from the proximal section of the main body the threaded nut is spread, allowing the threaded rod to move freely without any conscious operation by the patient, with screwing together of both sections of the main body after replacement of the ampoule easily causing a premature unintentional discharge of fluid. Depending on the injection device, this could also result in an incorrect dosing which, in case of certain medication, could prove extremely hazardous to the patient's health.

The invention aims to remedy this situation. It is the object of the invention to provide an injection device in which the sliding back of the driven member requires a conscious operation by the patient, which releases the driven member and counter component from each other to prevent the hazard of an incorrect dosing.

The invention solves the set task by an injection device with a driven member which can be shifted freely in axial direction by forcibly opening the counter component.

The advantages achieved by the invention lie mainly in the fact that the free return of the driven member is only possible when the patient releases the driven member by activation of a slide, i.e. by a conscious additional operation.

A preferred embodiment of the invention is shown in the figures, where:

In the subsequent description, the terms proximal and distal are used in their usual medical sense, i.e. proximal=facing the patient and distal=facing away from the patient.

Figure 1:
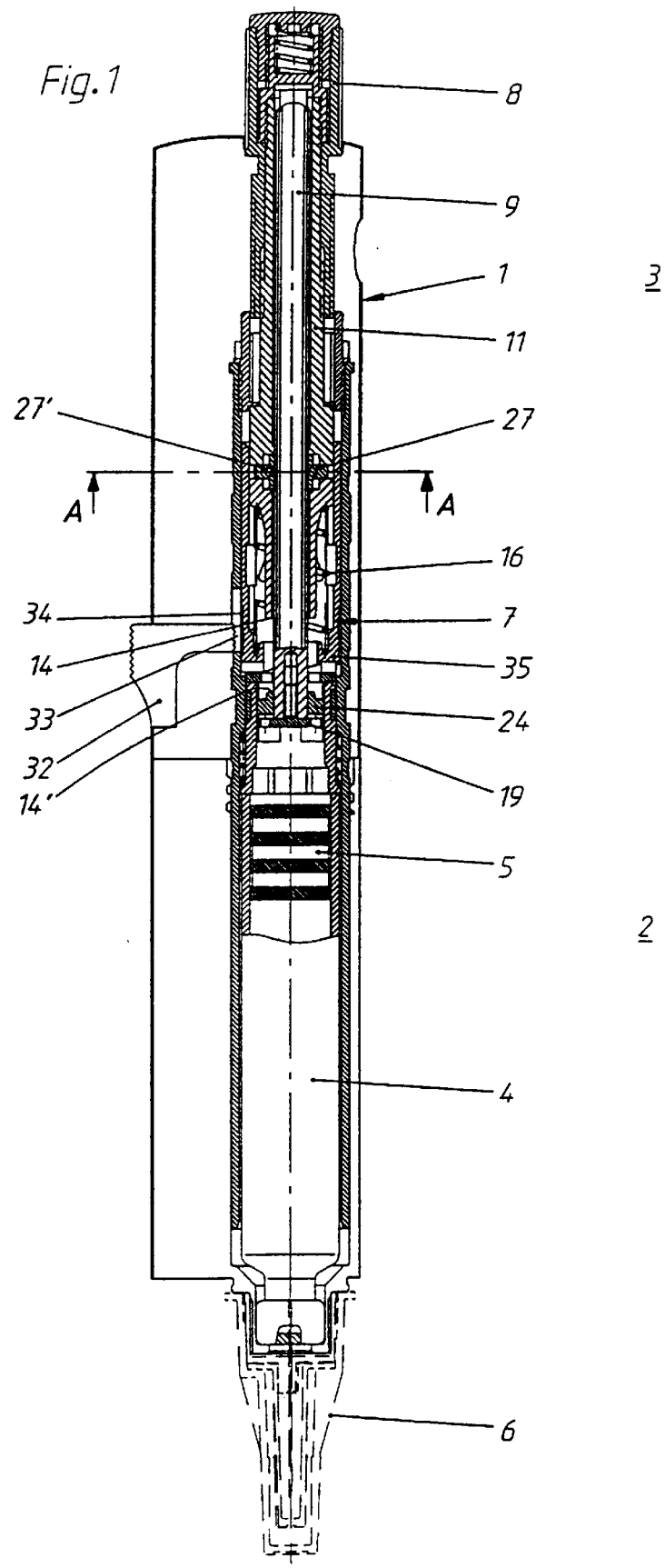
FIG. 1 shows an injection device according to the invention with a retained threaded rod.

As shown in FIG. 1, the injection device according to the invention comprises a bushing-shaped main body 1 which can be divided into a rear (distal) section 3 containing the tubular actuating device or discharge mechanism 7 and a front (proximal) section 2 containing a replaceable ampoule 4 and a piston 5. A needle 6 with its distal end connected to the fluid to be administered can be screwed to the proximal end of the main body 1. The actuating device 7 comprises a control button 8, a threaded rod 9 with a flange 19, a guide member 24 and a driving member 11.

The tubular driving member 11 is rigidly connected to the control button 8 to prevent twisting. At the proximal end, the driving member 11 surrounds two threaded flanges 27, 27' engaging in the thread of the threaded rod 9.

Figure 5:
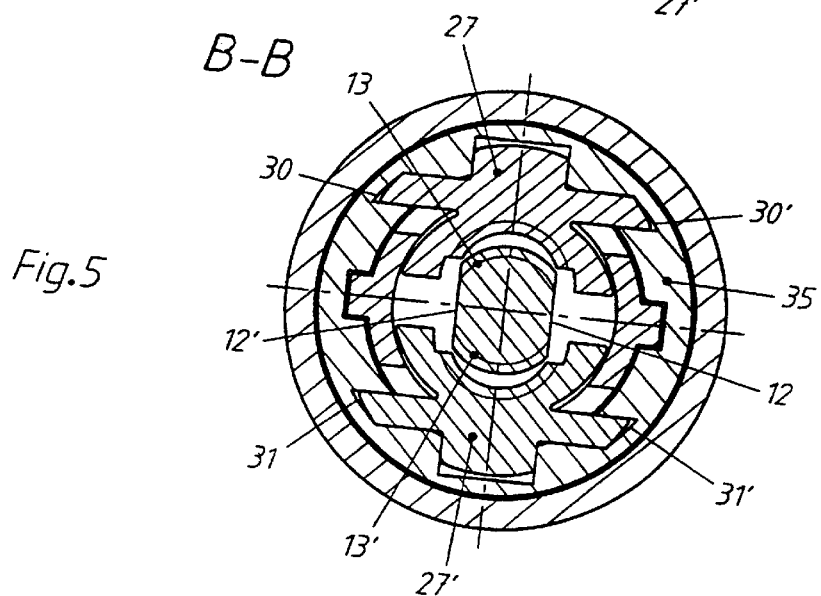
FIG. 5 shows a cross section along line B—B.

FIG. 5 shows that the threaded rod 9 comprises two level surfaces 12, 12' and apart from that is of a circular cross section, with the circular surfaces 13, 13' being threaded.

Figure 6:
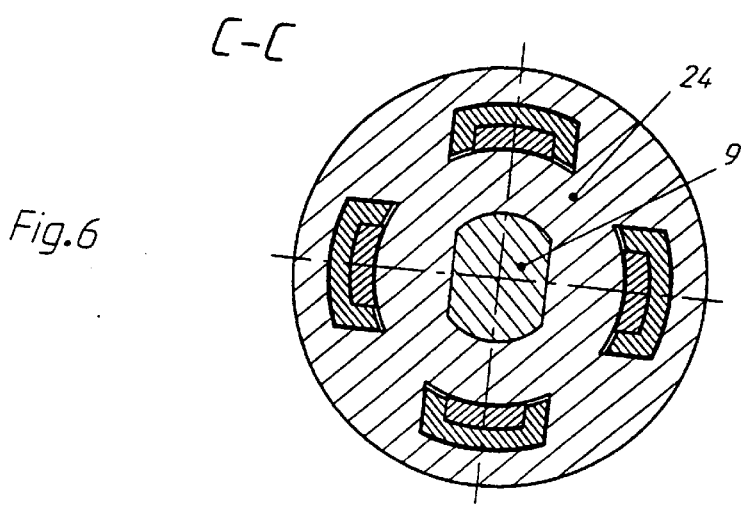
FIG. 6 shows a cross section along line C—C.

The guide member 24 is rigidly connected to the distal section 3 of the main body 1, thus preventing rotation or axial movement and is positioned in front of the driving member 11. The aperture in the guide member 24, through which the threaded rod 9 passes (FIG. 6) is of the same cross section as the threaded rod 9—although enlarged by certain tolerances. As the guide member 24, in contrast to the driving member 11, is not threaded, the threaded rod 9 can be shifted to and fro through the opening of the guide member in axial direction. A rotational movement of the threaded rod 9 is therefore not possible as the guide member 24 does not allow this.

The control button 8 may be moved in axial direction or may be rotated. Where the control button is activated by being pushed in proximal direction, it will simultaneously shift the driving member 11 until its front face 14 pushes against the rear face 14' of the guide member.

The threaded rod 9 is connected to the driving member 11 by threaded flanges 27, 27' thus allowing any axial movement of the control button 8 to be transferred. See detailed description of threaded flanges 27, 27' below.

The axial movement is effected against the bias of a spring 16, returning the actuating device 7 to its home position (FIG. 1).

When turning the control button 8 to adjust an injection dose, the driving member 11 is also turned. This rotating movement can, however, not be transferred to the threaded rod 9 as the rod is rigidly seated in the guide member 24. As a result of the rotating threaded flanges 27, 27' in driving member 11, the threaded rod 9 is rigidly driven forward via the threaded sections of the circular surfaces 13, 13' (or backward, when reversing the rotation direction of the control button), thus bringing the flange 19 into the position required for the next injection dose to be discharged, i.e. the distance of the flange 19 from the piston 5 is respectively reduced.

By pressing the control button 8, the actuating device 7 is moved from its home position to the end position. The flange 19 pushes thereby against the piston 5 during this operation, carrying it along the set piston travel and thus discharging the pre-set volume of injection fluid through injection needle 6. The travel of the flange 19 from the home position to the end position of the actuating device 7 always remains the same and corresponds to a constant distance by which the flange 19 is separated from the piston 5 before setting the injection dose. This process is described in detail in WO 93/16740.

When the fluid container 4 is empty and the threaded rod 9 is therefore in the extreme proximal position, the threaded rod must be returned to the extreme distal position. The injection device according to the invention allows the threaded rod 9 to be returned by activation of an unlocking slide 32.

Figure 4:
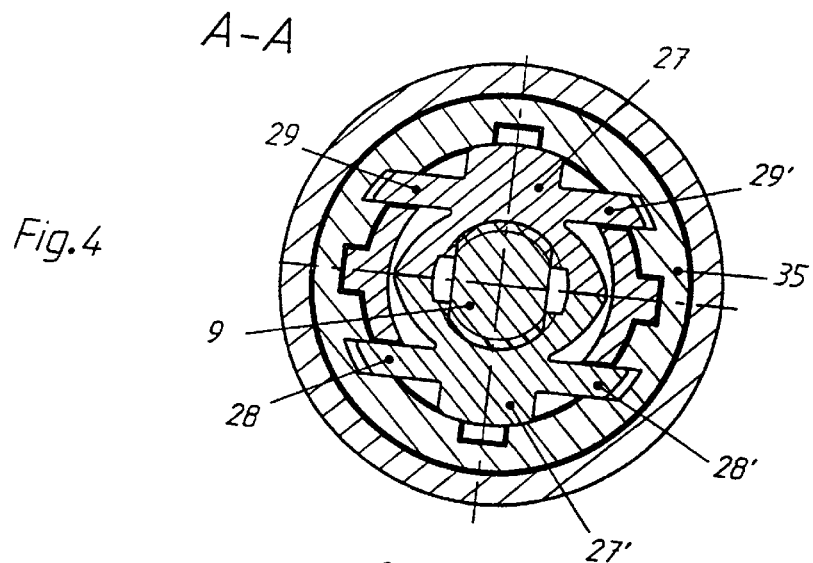
FIG. 4 shows a cross section along line A—A.

FIGS. 4 and 5 show that both threaded flanges 27, 27' of the driving member 11 are designed as two half-shell threaded nut sections, each provided with two cams 28, 28', 29, 29'.

The unlocking slide 32 attached to the rear section 3 is connected to an internal spreader bushing 35 in the rear section 3, with shifting of the unlocking slide 32 in distal direction causing the spreader bushing 35 to be shifted in distal direction.

The spreader bushing 35 surrounds the driving member 11 and comprises four vertical tracks 30, 30', 31, 31' (FIG. 3), which extend towards the proximal end of the spreader bushing 35 outwardly at an angle. The tracks 30, 30', 31, 31' serve to accommodate the cams 28, 28', 29, 29' of the threaded flanges 27, 27'. When the spreader bushing 35 is in the proximal position (FIG. 1), the threaded flanges 27, 27' surround the threaded rod 9. When the spreader bushing 35 is moved to its distal position (FIG. 2) with the unlocking slide 32, the threaded flanges 27, 27' open as soon as their cams 28, 28', 29, 29' move over the angled section of the tracks 30, 30', 31, 31' and the threaded rod 9 can be freely shifted in axial direction.

A notched surface 33 of the unlocking slide 32 arranged on the main body fits into a counter notched surface 34 on the proximal part of the spreader bushing 35.

Figure 3:
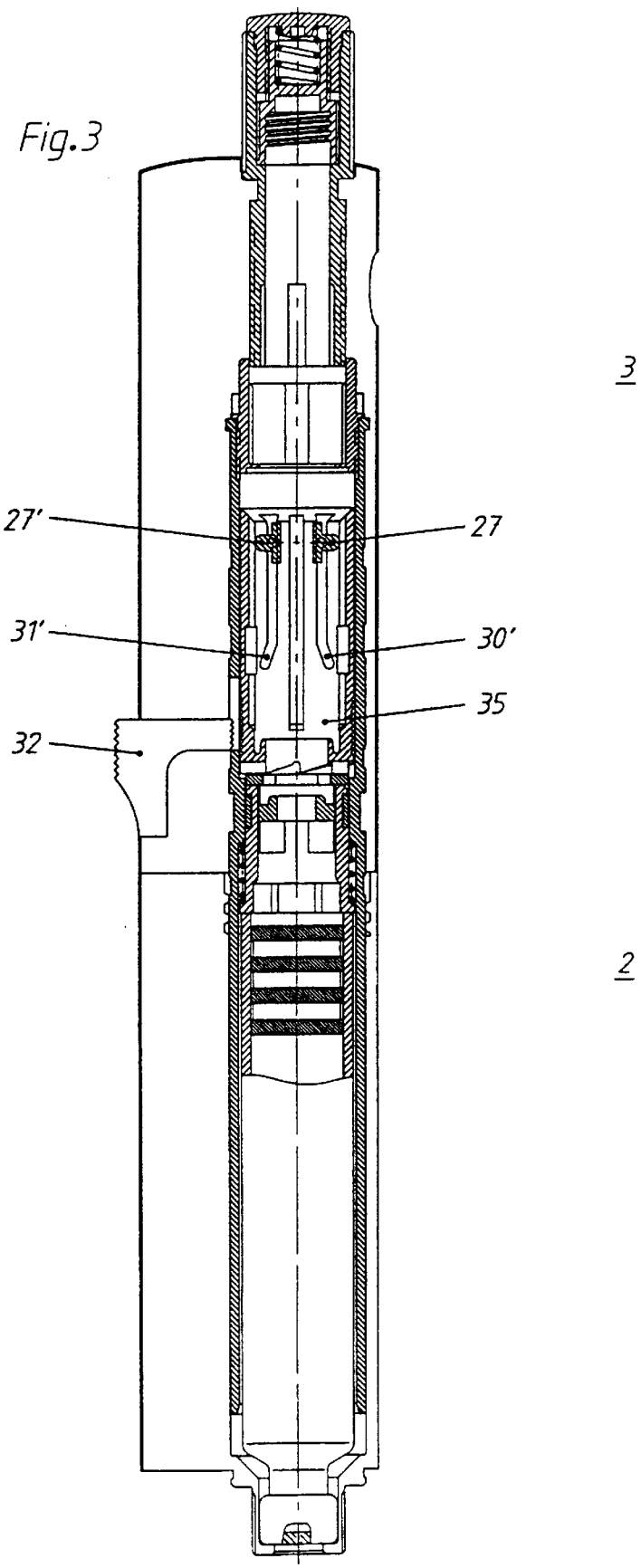
FIG. 3 shows an injection device according to the invention in which the actuating device has been removed.

In principle, the spreader bushing 35 is retained in its proximal position by the spring 16. In order to release the threaded flange 27, 27' the user must actively shift the unlocking slide 32 into its distal position by simultaneous pushing it down. During this process, the notched surface 33 of the unlocking slide 32 engages in the counter notched surface 34 of the spreader bushing 35, moving it backwards. Because of this movement, the cams 28, 28', 29, 29' must run over corresponding outwardly extending tracks 30, 30', 31, 31' of the spreader bushing 35 (FIGS. 3–5). This forced movement causes the threaded flanges 27, 27' to open (FIG. 5) and releases the threaded rod 9. When at the same time the injection device is held with the dosing button 8 down, gravity causes the threaded rod 9 to automatically fall back into its distal position. Upon releasing the unlocking slide 32, the spreader bushing 35 slides forward again. At the same time the cams 28, 28', 29, 29' slide back in the tracks 30, 30', 31, 31' to their stop position in which the threaded flange 27, 27' is closed. The unlocking slide 32 is moved into the proximal position by means that are not shown.

Figure 2:
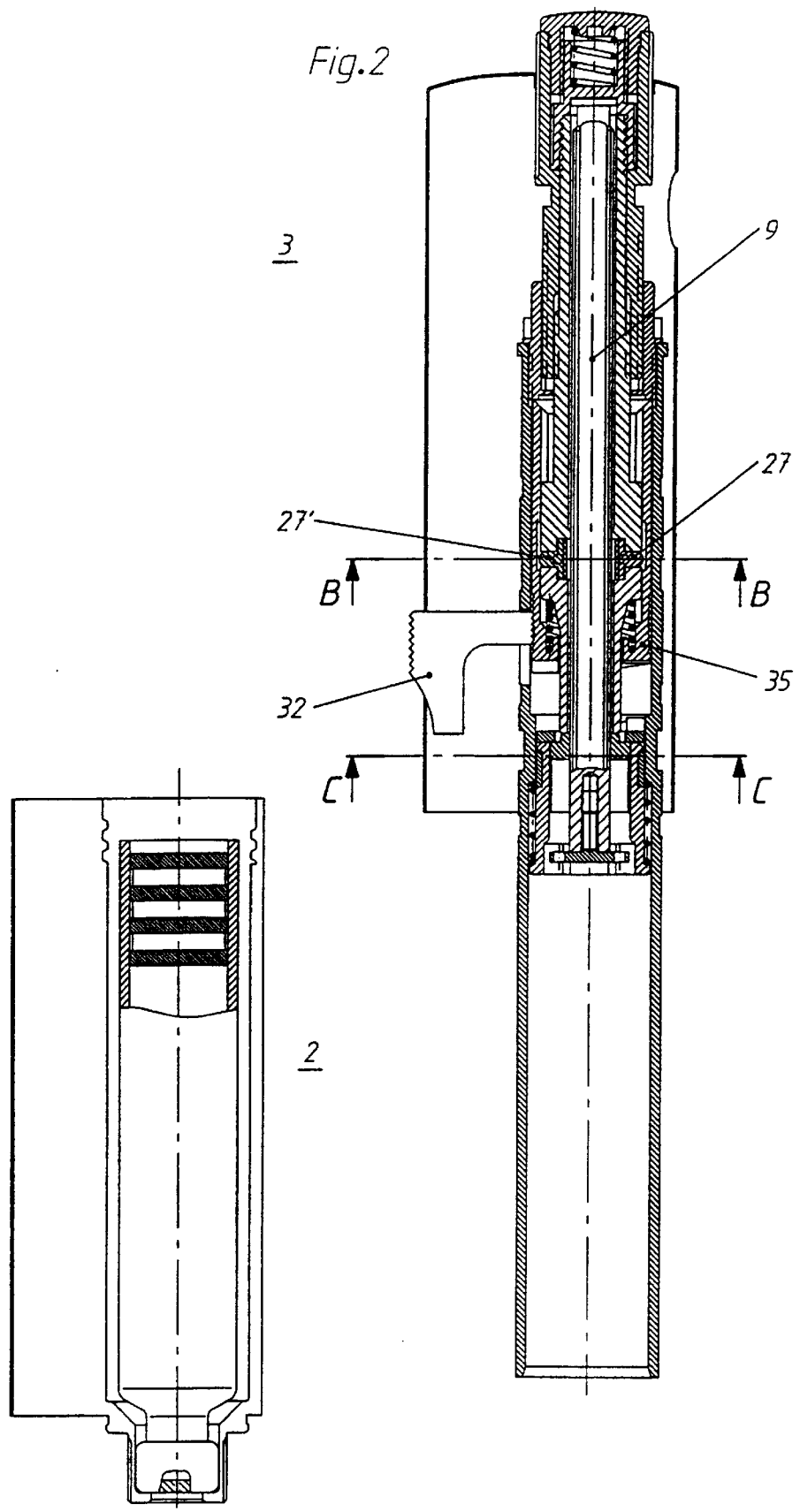
FIG. 2 shows an injection device according to the invention with a free threaded rod.

For safety reasons, the threaded flanges 27, 27' can only be released from the threaded rod 9 with the actuating device 7 in its proximal position (FIG. 2). For this reason the tracks 30, 30', 31, 31' are of such a dimension that activation of the unlocking slide 32 in the operating position of the actuating device 7 (FIGS. 1 and 3) only causes the cams 28, 28', 29, 29' to slide in the vertical tracks 30, 30', 31, 31' without reaching their angled section at the proximal end of the spreader bushing 35. In order for the cams 28, 28', 29, 29' to reach the angled section of the tracks 30, 30', 31, 31' and to release themselves from the threaded rod 9, the actuating device must also be in its proximal position (FIG. 2).

Simpler types of driving mechanisms in which the driving member 11 is not designed as a threaded rod 9 but contains a saw-tooth-type structure could also be imagined.

We claim:

1. An injection device for injecting fluid from a fluid container equipped with a piston, comprising an actuating device having a rod-shaped driven member having a structured surface, a control button being movable in axial direction and a hollow cylindrical counter component having a structured internal sleeve, said structured sleeve engaging said structured surface of the rod-shaped driven member wherein said driven member is advanceable by said actuating device and being coaxially arranged in relation to said driven member, characterised in that the counter component is spread open by a spreader bushing allowing the driven member to shift freely therein in axial direction.

2. The injection device according to claim 1, characterised in that the counter component is opened by an axial movement of the spreader bushing.

3. The injection device according to claim 2, characterised in that the counter component comprises two shell sections provided with cams running in the tracks of the spreader bushing.

4. An injection device for injecting fluid from a fluid container equipped with a piston, comprising an actuating device having a rod-shaped driven member having a structured surface, a control button being movable in axial direction and a hollow cylindrical counter component having a structured internal sleeve, said structured sleeve engaging said structured surface of the rod-shaped driven member wherein said driven member is advanceable by said actuating device and being coaxially arranged in relation to said driven member, characterised in that the counter component comprises two shell sections and is spread open by an axial movement of a spreader bushing with a proximal area and a distal area and tracks, thereby allowing the driven member to shift freely therein in an axial direction, said shell sections provided with cams running in the tracks of the spreader bushing, said tracks of the spreader bushing vertical in the proximal area and angled in the distal area.

5. The injection device according to claim 4, characterised in that the driven member comprises threaded surfaces and level surfaces, the level surfaces being on two facing sides and apart from the threaded surfaces.

6. The injection device according to claim 5, characterised in that the surface of the driven member and the internal sleeve of the shell sections are threaded.

7. The injection device according to claim 6, characterised in that the shell sections can only be opened when the shell sections are in proximal position.

8. The injection device according to claim 7, characterised in that the spreader bushing can be connected to an unlocking slide.

9. The injection device according to claim 8, characterised in that the surface of the driven member is provided with toothed or ribbed structures and that the internal sleeve of the counter component is provided with structures corresponding thereto.

* * * * *